United States Patent [19]
Schreiner et al.

[11] Patent Number: 5,661,242
[45] Date of Patent: Aug. 26, 1997

[54] PROCESS AND APPARATUS FOR THE ULTRASONIC TESTING OF A COMPONENT ACCESSIBLE ONLY THROUGH A GAP

[75] Inventors: Klaus Schreiner, Speyer; Leonhard Knieriem, Erbach, both of Germany

[73] Assignee: ABB Reaktor GmbH, Mannheim, Germany

[21] Appl. No.: 576,096

[22] Filed: Dec. 21, 1995

[30] Foreign Application Priority Data

Dec. 21, 1994 [DE] Germany .......................... 44 45 696.4
Mar. 3, 1995 [DE] Germany ........................ 195 07 393.2

[51] Int. Cl.$^6$ ........................ G01N 29/24; G01N 29/04
[52] U.S. Cl. .................. 73/623; 73/622; 73/624; 73/628; 73/634; 376/249; 376/252
[58] Field of Search .................... 376/245, 249, 376/252; 976/DIG. 211, DIG. 212, DIG. 214; 73/618, 619, 620, 621, 622, 623, 624, 627, 628, 629, 632, 634, 637

[56] References Cited

U.S. PATENT DOCUMENTS

| | | | |
|---|---|---|---|
| 4,383,448 | 5/1983 | Fujimoto et al. | 73/637 |
| 4,472,346 | 9/1984 | Takeda et al. | 376/246 |
| 4,569,230 | 2/1986 | Asty et al. | 73/623 |
| 4,752,435 | 6/1988 | Fenemore et al. | 376/249 |
| 5,068,721 | 11/1991 | Dietrich | 376/248 |
| 5,156,050 | 10/1992 | Schmid et al. | 73/628 |
| 5,327,079 | 7/1994 | Haller et al. | 376/249 |

FOREIGN PATENT DOCUMENTS

| | | |
|---|---|---|
| 0 242 136 | 10/1987 | European Pat. Off. . |
| 0 445 506 | 9/1991 | European Pat. Off. . |
| 2186709 | 1/1974 | France . |
| 28 30 908 | 1/1980 | Germany . |
| 35 24 390 | 1/1987 | Germany . |
| 40 05 545 | 8/1991 | Germany . |
| 42 15 700 | 11/1993 | Germany . |
| 92/07363 | 4/1992 | WIPO . |

OTHER PUBLICATIONS

Patent Abstract of Japan No. JP 2-116,747, Masaru et al., May 1, 1990.

*Primary Examiner*—Hezron E. Williams
*Assistant Examiner*—Rose M. Miller
*Attorney, Agent, or Firm*—Herbert L. Lerner; Laurence A. Greenberg

[57] ABSTRACT

A process and an apparatus for the ultrasonic testing of a component accessible only through a gap, includes driving a carrier accommodating an ultrasonic testing head into an annular gap and bringing the ultrasonic testing head into a position of alignment with the component, for the purposes of repeated testing of components disposed in the poorly accessible gap. Subsequently, the ultrasonic testing head is driven out from the carrier approximately at right angles to the driving-in movement, and is brought into contact with the component. After completing the testing process, the ultrasonic testing head is driven once more into the carrier and brought into a position of alignment with the next component.

8 Claims, 3 Drawing Sheets

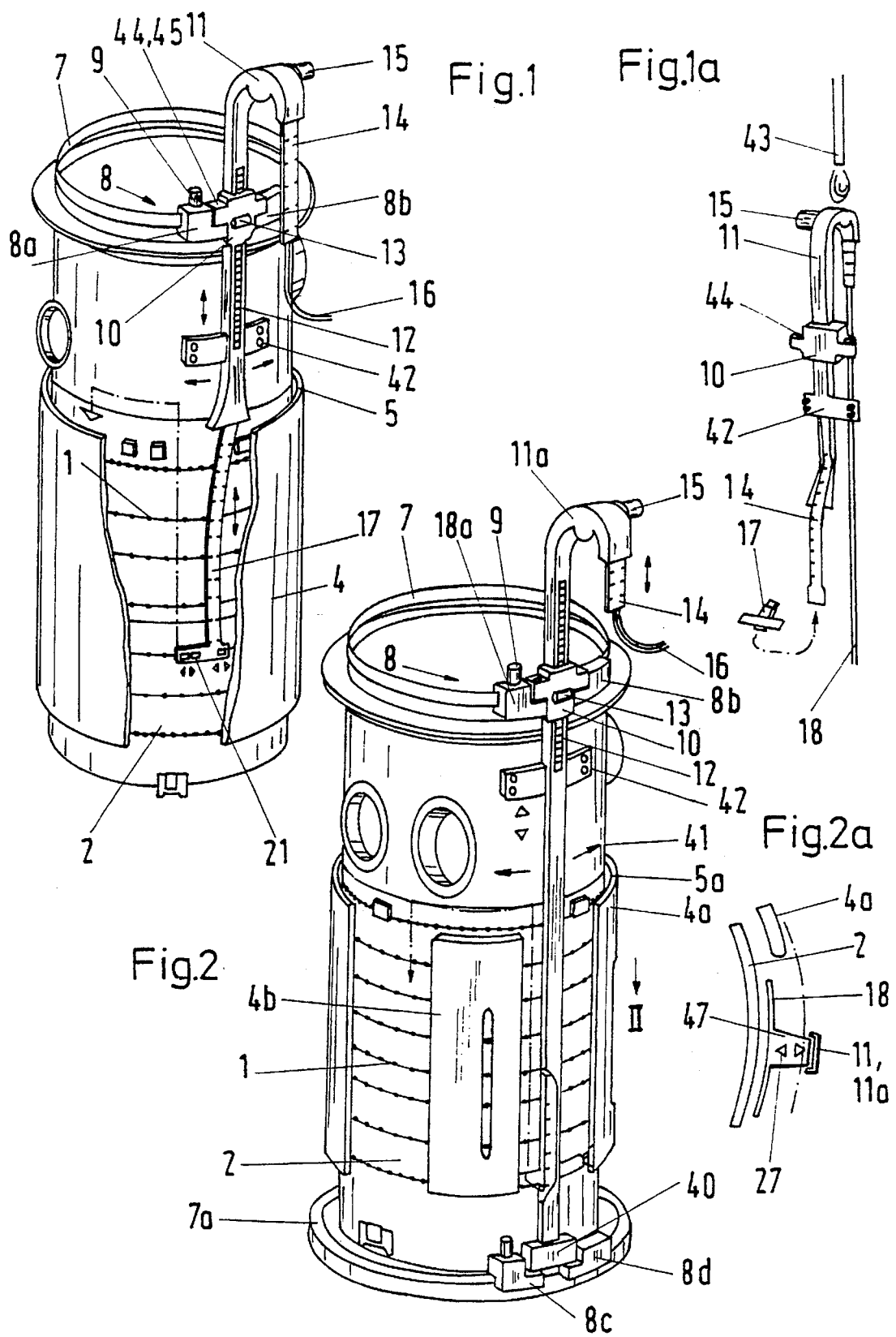

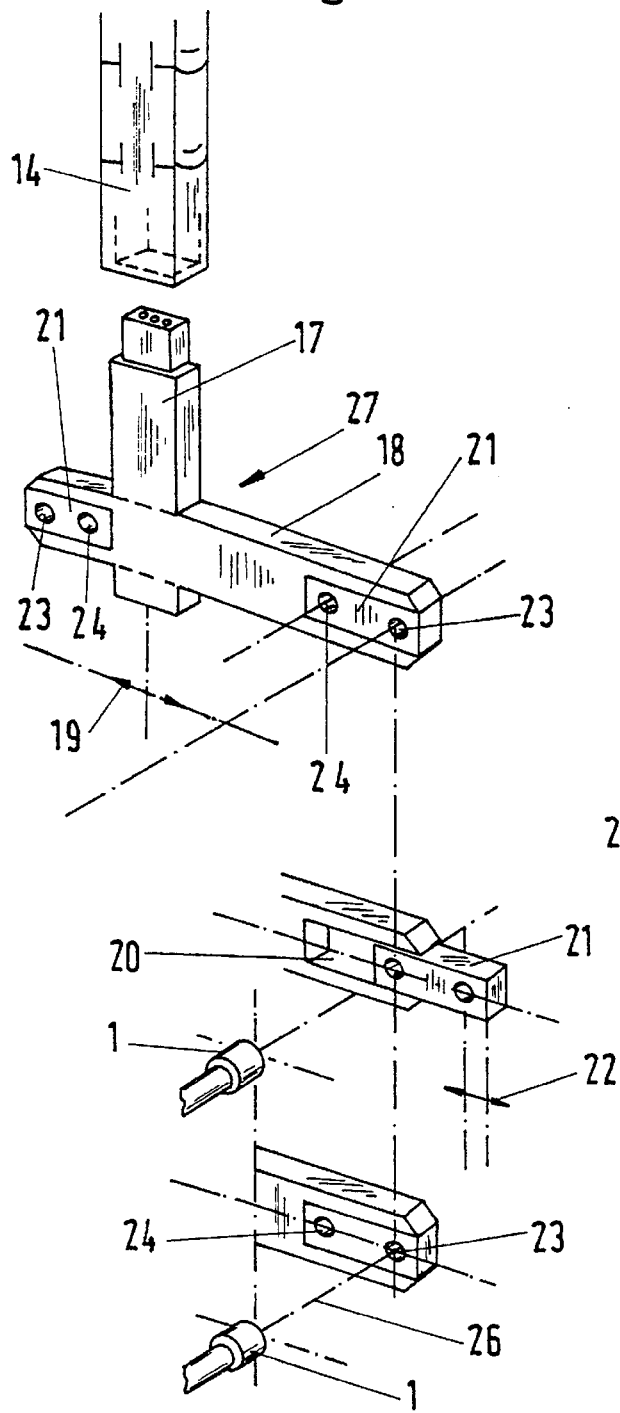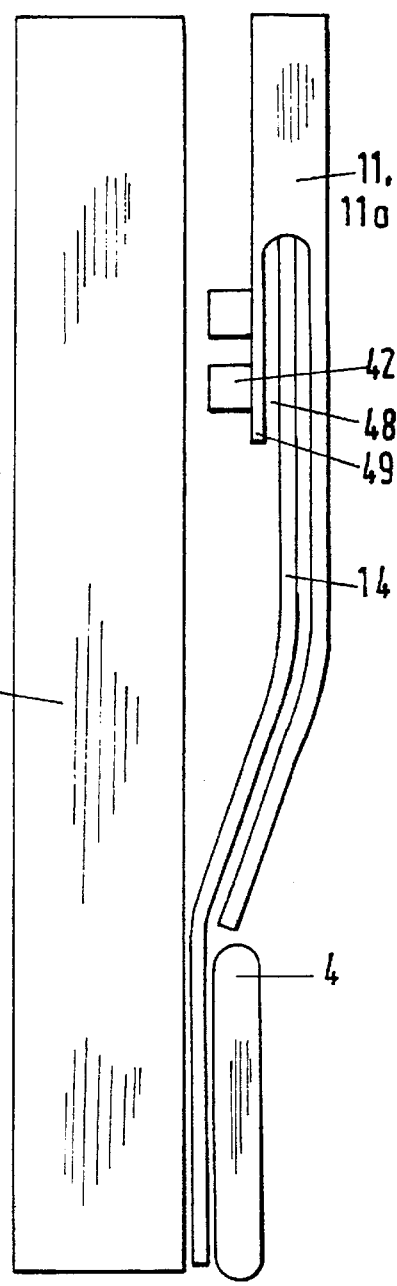

PROCESS AND APPARATUS FOR THE ULTRASONIC TESTING OF A COMPONENT ACCESSIBLE ONLY THROUGH A GAP

BACKGROUND OF THE INVENTION

FIELD OF THE INVENTION

The invention relates to a process and an apparatus for the ultrasonic testing of a component being accessible through a gap and associated with a wall bounding the gap.

Heretofore, components such as securing screws, for example, that were disposed in such a gap were not subjected to repeated testing because of difficult accessibility. However, in the case of relevant industrial installations, more recent safety regulations require the testing of those components previously considered as poorly accessible.

SUMMARY OF THE INVENTION

It is accordingly an object of the invention to provide a process and an apparatus for the ultrasonic testing of a component accessible only through a gap, which overcomes the hereinafore-mentioned disadvantages of the heretofore-known processes and an apparatuses of this general type.

With the foregoing and other objects in view there is provided, in accordance with the invention, a process for the ultrasonic testing of a component being accessible only through a gap and being associated with a wall bounding the gap, which comprises driving a carrier accommodating an ultrasonic testing head into a gap in a given driving-in direction; bringing the ultrasonic testing head into a position of alignment with the component by driving the ultrasonic testing head out of the carrier in the direction of the component and approximately at right angles to the given driving-in direction; irradiating the component with sound; and driving the ultrasonic testing head into the carrier and bringing the ultrasonic testing head into a position of alignment with the next component to be tested, after completion of a testing process.

With the objects of the invention in view, there is also provided, in an assembly having an outer circumferentially closed cylinder and an inner circumferentially closed cylinder projecting beyond the outer cylinder in axial direction and defining a gap between the cylinders, an apparatus for the ultrasonic testing of a component being accessible only through the gap, comprising an annular rail disposed above the inner cylinder; a carriage to be driven along the annular rail; a sliding body associated with the carriage; a guide rail penetrating the sliding body, being movable relative to the sliding body and ending above the outer cylinder; a probe body to be driven into the gap in a given direction and to be moved along the guide rail, the probe body having an end piece facing the gap; a side rail disposed on the end piece of the probe body for being driven transversely to the given direction, the side rail having ends; a carrier being disposed at least at one of the ends of the side rail and being movable in axial direction of the side rail; and an ultrasonic testing head being carried by the carrier and being controlled for movement running relative to the carrier.

With the objects of the invention in view, there is additionally provided, in an assembly having an outer cylinder formed of mutually spaced apart cylindrical part-shells and an inner cylinder projecting beyond the outer cylinder and defining a gap between the cylinders, an apparatus for the ultrasonic testing of a component being accessible only through the gap, comprising a first annular rail disposed above the inner cylinder; a carriage to be driven along the annular rail; a sliding body being associated with the carriage; a guide rail penetrating the sliding body, being movable relative to the sliding body and being extended as far as beneath the outer cylinder; a second annular rail; a sliding element supporting the guide rail on the second annular rail; a probe body to be driven into the gap in a given direction and to be moved along the guide rail, the probe body having an end piece facing the gap; a side rail being disposed on the end piece of the probe body for being driven transversely to the given direction, the side rail having ends; a carrier being disposed at least at one of the ends of the side rail and being movable in axial direction of the side rail; and an ultrasonic testing head being carried by the carrier and being controlled for movement running relative to the carrier.

Since the ultrasonic testing head can be driven completely into the carrier, the carrier can be constructed to be relatively thick even in the case of narrow gaps, so that stability is ensured. Such stability is also necessary when, after reaching the alignment position (the ultrasonic testing head and the object to be tested are located in one testing plane), the testing head is driven-out in the direction of the object to be tested.

In accordance with another feature of the invention, the guide rail has a tang being disposed above the outer cylinder and facing the inner cylinder, and there is provided a calibration body disposed on the tang, for bringing the ultrasonic testing head on the side rail into position opposite the calibration body.

In accordance with a further feature of the invention, the carriage includes two part-carriages being connected to each other by the sliding body.

In accordance with an added feature of the invention, there is provided a camera being associated with the carrier and disposed at a predeterminable distance from the ultrasonic testing head, the ultrasonic testing head and the camera lying on the same axis of symmetry as seen in axial direction of the side rail.

In accordance with a concomitant feature of the invention, the carrier has a shoulder; and the ultrasonic testing head being movable relative to the carrier has an annular diaphragm with an inner edge region and an outer edge region; a cover plate being let into the carrier and pressing the outer edge region of the annular diaphragm against the shoulder of the carrier; a bellows having a flange facing away from the cover plate and having a flanged bush facing the cover plate and being connected to the inner edge region of the diaphragm, the flange of the bellows carrying at least one ultrasonic oscillator; the diaphragm and the cover plate defining a chamber therebetween alternatively having pressure and a vacuum applied to the chamber; and the bellows having an internal space being connected to the chamber through an opening.

Other features which are considered as characteristic for the invention are set forth in the appended claims.

Although the invention is illustrated and described herein as embodied in a process and an apparatus for the ultrasonic testing of a component accessible only through a gap, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic, partly broken-away perspective view of built-in components of a core of an industrial nuclear installation with a testing apparatus;

FIG. 1a is a perspective view of part of the apparatus according to FIG. 1;

FIG. 2 is a view similar to FIG. 1 showing another structure of the configuration according to FIG. 1;

FIG. 2a is an elevational view showing a part of FIG. 2, as seen in the direction of an arrow II;

FIG. 3 is a longitudinal-sectional view of part of the built-in components of the core and of the testing apparatus;

FIG. 4 is an enlarged, fragmentary, exploded, perspective view showing a part of the testing apparatus.

DESCRIPTION OF THE PREFERRED EMBODIMENTS

Figure 5:
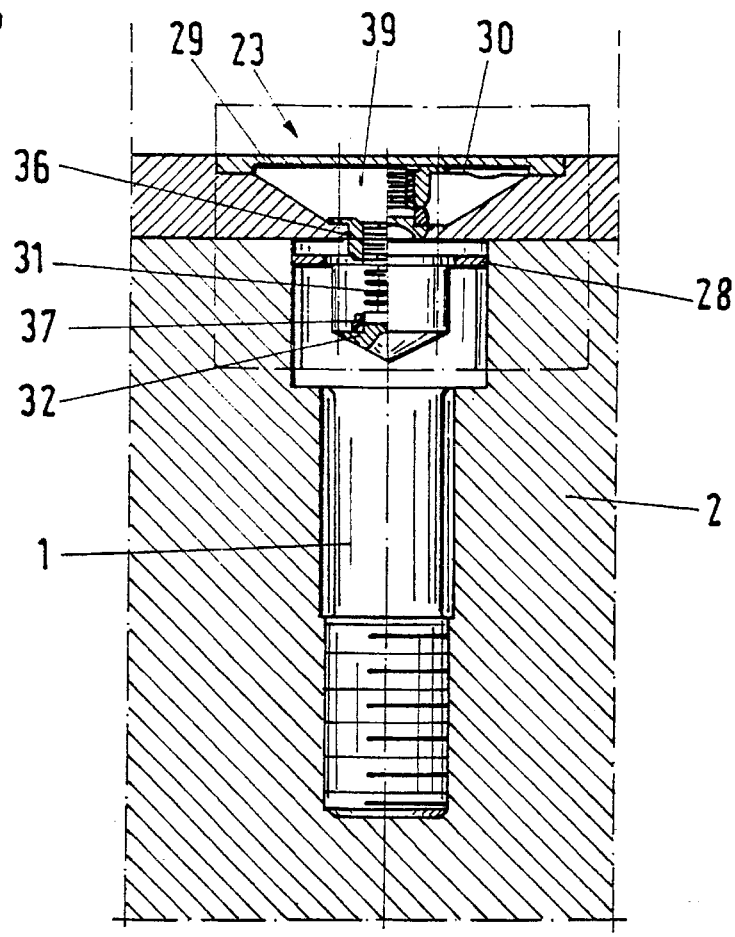
FIGS. 5 and 5a are partly broken-away perspective views showing an ultrasonic testing head for carrying out the process.

Referring now to the figures of the drawing in detail and first, particularly, to FIG. 1 thereof, there is seen a perspective representation of an inner cylinder 2 which acts as a core container belonging to built-in components of a core of a non-illustrated industrial nuclear installation. The inner cylinder 2 has a lower region which is surrounded by an outer cylinder 4 while maintaining an annular gap 5. The outer cylinder 4 acts as a thermal shield for the built-in components of the core and is constructed as a closed hollow cylinder. A cut-away section of the outer cylinder 4 exposes a view of the inner cylinder 2 and the components 1 disposed there. In this exemplary embodiment a component 1 of this type forms a hexagonal socket screw, shown on a larger scale in FIG. 5, which is let into the wall of the inner cylinder 2. For the purposes of testing such a component, a first annular rail 7 above the inner cylinder 2 projects beyond the outer cylinder 4 in the axial direction. The annular rail 7 carries a carriage 8 which can be moved along the annular rail 7 with the aid of a drive 9. A sliding piece 10 which is penetrated by a guide rail 11 is assigned to the carriage 8. The guide rail 11 ends above the outer cylinder 4. The guide rail 11 has a tooth system 12 of rack-like construction and can be moved relative to the carriage 8 to a predeterminable extent through a drive 13 engaging in the tooth system. A resilient probe body 14 can be moved along the guide rail 11 by a drive 15 which is disposed in a curve piece of the guide rail 11. A power supply is provided through a cable 16. The probe body 14 has a free end at which an end piece 17 (also seen in FIGS. 1a and 4) is disposed and connected to it detachably. The carriage 8 includes two part carriages 8a, 8b, which are connected to each other by the sliding piece 10. As can be seen from FIG. 1a, the sliding piece 10, together with the guide rail 11 and the probe body 14, can be separated from the remaining carriage parts 8a, 8b with the aid of lifting gear 43. In the assembled state, holes 44 associated with the sliding piece 10 engage pins 45 which are fitted on the carriage parts 8a, 8b. The apparatus is provided with a variable structure by using this carriage which is constructed in three parts. A sliding piece 10 which is equipped with another guide rail 11 or another probe body 14 can be inserted in a simple manner, so that other testing tasks can be carried out on the cylinders 2 and 4.

As can be seen further from FIG. 4, which is shown on a larger scale, the end piece 17 has a side rail 18 assigned to it which can be moved in the direction of an arrow 19 by a non-illustrated drive. The side rail 18 has free ends with a guide 20. A carrier 21 can be moved in the direction of an arrow 22 in each guide 20. Each carrier 21 is equipped with an ultrasonic testing head 23 which is shown on a larger scale in FIGS. 5 and 5a. The carrier 21 has a camera 24 at a predeterminable distance from the ultrasonic testing head 23. The camera 24 and the ultrasonic testing head 23 are disposed along an axis of symmetry 25 running parallel to the longitudinal extension of the side rail 18.

FIG. 4 also shows measures which are necessary for placing the ultrasonic testing head 23 on an alignment line 26. After driving the carrier 21 into the annular gap 5 by using the elements described with regard to FIG. 1, and after a successful centering between the camera 24 and the component 1 constructed as a hexagonal socket screw, a displacement of the carrier 21 is carried out in the direction of the arrow 22 by a predetermined distance between the camera and the ultrasonic testing head, so that the precise positioning on the alignment line 26, which can be seen from FIG. 4, is carried out.

After this positioning on the alignment line has been achieved, the driving of the carrier 21 in the direction of an arrow 27, according to FIGS. 2a and 4, is carried out until a wall of the inner cylinder 2 which is accommodating the component 1 to be tested is contacted by the carrier 21. According to FIG. 2a, a remotely-controllable plunger 47 which is used for this purpose can be adjusted against the guide rail 11, 11a and as a result permits a movement of the carrier 21 until it rests on the wall.

Figure 5A:
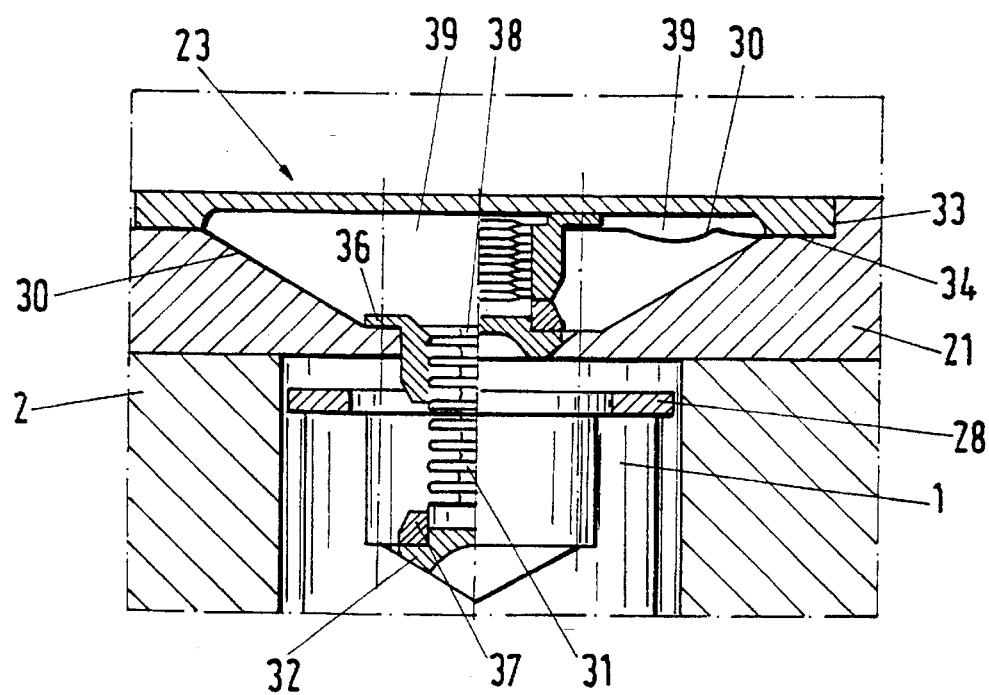

The hexagonal socket screw which is to have sound passed through it to look for cracks is secured by using a disc 28 shown in FIGS. 5 and 5a, so that the testing can be carried out only through the bottom surface of the hexagonal socket. As can be seen more clearly from FIGS. 5 and 5a, which are shown on a larger scale, the ultrasonic testing head, which is designated as a whole by reference numeral 23, includes a cover plate 29 that is let into the carrier 21, a diaphragm 30, a bellows 31 and at least one ultrasonic transducer which is assigned to a flange 37 of the bellows 31. The diaphragm 30, which is of annular construction, is clamped with its outer edge region 33 between the cover plate 29 and a shoulder 34 of the carrier 21. The diaphragm 30 has an inner edge region 35 which is fastened on a flanged bush 36 of the bellows 31. A contact piece 32 made of a resilient material is disposed between the flange 37 carrying at least one ultrasonic transducer and a surface of the specimen or component. Through the use of a corresponding recess in the carrier 21, a chamber 39 is formed between the cover plate 29 and the diaphragm 30. The chamber 39, including an internal space of the bellows 31, which is accessible through an opening 38, can alternatively have pressure (left drawing half) or a vacuum (right drawing half) applied to it. If a vacuum is applied, the entire ultrasonic testing head 23 is located inside the carrier 21, in a manner similar to the right drawing half. This position of the ultrasonic testing head 23 is assumed during driving movements of the carrier 21 within the annular gap and protects the ultrasonic testing head from damage. When the testing position according to FIGS. 5 and 5a is reached, the chamber 39 has pressure applied to it. In a manner similar to the left drawing half of FIGS. 5 and 5a, the flange 37, carrying the at least one ultrasonic transducer, is driven out until the resilient contact piece 32 comes to rest on the bottom surface of the hexagonal socket of the screw. The bellows 31 and the chamber 39 permit an extended length of the ultrasonic testing head 23 which can be greater than the thickness of the carrier 21. Since the diaphragm and the bellows do not need separate seals, no sealing problems can occur. The bellows leads to a flexible and self-centering apparatus. After the testing has been carried out, a vacuum is applied to the chamber 39, so that the ultrasonic testing head 23 once more assumes the position shown in the right drawing half. According to FIG. 1, the next position to be tested is driven to by using the drive 15 and the carriage 8 and is finely adjusted with the aid of the side rail 18 and the carrier 21. The exemplary embodiment according to FIG. 2 is a perspective diagrammatic view of an inner container 2 which acts as a core container and belongs to built-in components of a core of a non-illustrated industrial nuclear installation. An outer cylinder 4a, acting as a thermal shield for the built-in components of the core, is formed of a plurality of cylindrical part-shells 4b which are spaced at intervals from one another. The part-shells 4b delimit an annular space 5a which, however, is interrupted because of the distance between the part-shells 4b. In the case of this configuration, a guide rail 11a extends as far as beneath the outer cylinder 4a. The guide rail 11a ends at a sliding element 40 which connects carriage parts 8c, 8d to each other. The carriage parts 8c, 8d are supported on a second annular rail 7a and can be moved along the same. The carriage 8, the sliding element 40 and the guide rail 11a connecting these components to one another carry out their rotational movement together with the aid of drives 9, 9a. The guide rail 11a accommodates the probe body 14 in a similar way to that described in relation to FIG. 1. The driving movement of the side rail 18 and/or the carriage is carried out in the direction of an arrow 41 in the annular space 5a delimited by the part-shells 4b. The testing of components 1 disposed in the annular space 5a such as, for example, a hexagonal socket screw, is carried out in the same way as described in relation to FIGS. 1, 4 and 5. Likewise, as in the case of the exemplary embodiment according to FIG. 1, the guide rail 11a, together with the sliding piece 10 and the sliding element 40, can be separated from the carriage parts.

According to FIGS. 1 and 2, a calibration body 42 is assigned to the guide rail 11, 11a. The carrier 21 with the ultrasonic testing head 23 can be brought into position opposite the calibration body and can be adjusted for faults and the like.

FIG. 3 shows a guide rail 11, 11a constructed partly with a slot 48. One tang 49 of the guide rail carries the calibration body 42 in the region of the slot 48. The probe body 14 is driven out until the carrier 21 with the ultrasonic testing head has passed in the slot 48 up to the level of the calibration body.

We claim:

1. In an assembly having an outer circumferentially closed cylinder and an inner circumferentially closed cylinder projecting beyond the outer cylinder in axial direction and defining a gap between the cylinders, an apparatus for the ultrasonic testing of a component being accessible only through the gap, comprising:

an annular rail disposed above the inner cylinder;

a carriage to be driven along said annular rail;

a sliding body associated with said carriage;

a guide rail penetrating said sliding body, being movable relative to said sliding body and ending above the outer cylinder;

a probe body to be driven into the gap in a given direction and to be moved along said guide rail, said probe body having an end piece facing the gap;

a side rail disposed on said end piece of said probe body for being driven transversely to said given direction, said side rail having ends;

a carrier being disposed at least at one of said ends of said side rail and being movable in axial direction of said side rail;

an ultrasonic testing head being carried by said carrier and being controlled for movement running relative to said carrier; and said guide rail having a tang being disposed above the outer cylinder and facing the inner cylinder, and including a calibration body disposed on said tang, for bringing said ultrasonic testing heads on said side rail into position opposite said calibration body.

2. The apparatus according to claim 1, wherein said carriage includes two part-carriages being connected to each other by said sliding body.

3. The apparatus according to claim 1, including a camera being associated with said carrier and disposed at a predeterminable distance from said ultrasonic testing head, said ultrasonic testing head and said camera lying on the same axis of symmetry as seen in axial direction of said side rail.

4. In an assembly having an outer cylinder formed of mutually spaced apart cylindrical part-shells and an inner cylinder projecting beyond the outer cylinder and defining a gap between the cylinders, an apparatus for the ultrasonic testing of a component being accessible only through the gap, comprising:

a first annular rail disposed above the inner cylinder;

a carriage to be driven along said annular rail;

a sliding body being associated with said carriage;

a guide rail penetrating said sliding body, being movable relative to said sliding body and being extended as far as beneath the outer cylinder;

a second annular rail;

a sliding element supporting said guide rail on said second annular rail;

a probe body to be driven into the gap in a given direction and to be moved along said guide rail, said probe body having an end piece facing the gap;

a side rail being disposed on said end piece of said probe body for being driven transversely to said given direction, said side rail having ends;

a carrier being disposed at least at one of said ends of said side rail and being movable in axial direction of said side rail;

an ultrasonic testing head being carried by said carrier and being controlled for movement running relative to said carrier; and said guide rail having a tang being disposed above the outer cylinder and facing the inner cylinder, and including a calibration body disposed on said tang, for bringing said ultrasonic testing head on said side rail into position opposite said calibration body.

5. The apparatus according to claim 4, wherein said carriage includes two part-carriages being connected to each other by said sliding body.

6. The apparatus according to claim 4, including a camera being associated with said carrier and disposed at a predeterminable distance from said ultrasonic testing head, said ultrasonic testing head an said camera lying on the same axis of symmetry as seen in axial direction of said side rail.

7. In an assembly having an outer circumferentially closed cylinder and an inner circumferentially closed cylinder projecting beyond the outer cylinder in axial direction and defining a gap between the cylinders, an apparatus for the ultrasonic testing of a component being accessible only through the gap, comprising:

an annular rail disposed above the inner cylinder;

a carriage to be driven along said annular rail;

a sliding body associated with said carriage;

a guide rail penetrating said sliding body, being movable relative to said sliding body and ending above the outer cylinder;

a probe body to be driven into the gap in a given direction and to be moved along said guide rail, said probe body having an end piece facing the gap;

a side rail disposed on said end piece of said probe body for being driven transversely to said given direction, said side rail having ends;

a carrier being disposed at least at one of said ends of said side rail and being movable in axial direction of said side rail, said carrier having a shoulder; and an ultrasonic testing head being carried by said carrier and being controlled for movement running relative to said carrier, said ultrasonic testing head being movable relative to said carrier having:

an annular diaphragm with an inner edge region and an outer edge region;

a cover plate being let into said carrier and pressing said outer edge region of said annular diaphragm against said shoulder of said carrier;

a bellows having a flange facing away from said cover plate and having a flanged bush facing said cover plate and being connected to said inner edge region of said diaphragm, said flange of said bellows carrying at least one ultrasonic oscillator;

said diaphragm and said cover plate defining a chamber therebetween alternatively having pressure and a vacuum applied to said chamber; and said bellows having an internal space being connected to said chamber through an opening.

8. In an assembly having an outer cylinder formed of mutually spaced apart cylindrical part-shells and an inner cylinder projecting beyond the outer cylinder and defining a gap between the cylinders, an apparatus for the ultrasonic testing of a component being accessible only through the gap, comprising:

a first annular rail disposed above the inner cylinder;

a carriage to be driven along said annular rail;

a sliding body being associated with said carriage;

a guide rail penetrating said sliding body, being movable relative to said sliding body and being extended as far as beneath the outer cylinder;

a second annular rail;

a sliding element supporting said guide rail on said second annular rail;

a probe body to be driven into the gap in a given direction and to be moved along said guide rail, said probe body having an end piece facing the gap;

a side rail being disposed on said end piece of said probe body for being driven transversely to said given direction, said side rail having ends;

a carrier being disposed at least at one of said ends of said side rail and being movable in axial direction of said side rail, said carrier having a shoulder; and an ultrasonic testing head being carried by said carrier and being controlled for movement running relative to said carrier, said ultrasonic testing head being movable relative to said carrier having:

an annular diaphragm with an inner edge region and an outer edge region;

a cover plate being let into said carrier and pressing said outer edge region of said annular diaphragm against said shoulder of said carrier;

a bellows having a flange facing away from said cover plate and having a flanged bush facing said cover plate and being connected to said inner edge region of said diaphragm, said flange of said bellows carrying at least one ultrasonic oscillator;

said diaphragm and said cover plate defining a chamber therebetween alternatively having pressure and a vacuum applied to said chamber; and said bellows having an internal space being connected to said chamber through an opening.

\* \* \* \* \*